US012635964B2

(12) United States Patent　　　　(10) Patent No.:　US 12,635,964 B2
Noda et al.　　　　　　　　　　　　(45) Date of Patent:　　May 26, 2026

(54) IMAGE PROCESSING APPARATUS, RADIOGRAPHIC IMAGING SYSTEM, IMAGE PROCESSING METHOD, AND STORAGE MEDIUM

(71) Applicant: CANON KABUSHIKI KAISHA, Tokyo (JP)

(72) Inventors: Takeshi Noda, Kanagawa (JP); Katsuro Takenaka, Saitama (JP); Satoshi Kamei, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 201 days.

(21) Appl. No.: 18/752,389

(22) Filed: Jun. 24, 2024

(65) Prior Publication Data

US 2024/0423572 A1　　Dec. 26, 2024

(30) Foreign Application Priority Data

Jun. 26, 2023　(JP) ................................. 2023-104348

(51) Int. Cl.
　　*A61B 6/00*　　　　(2024.01)
　　*A61B 6/50*　　　　(2024.01)
(52) U.S. Cl.
　　CPC ............ *A61B 6/5205* (2013.01); *A61B 6/482* (2013.01); *A61B 6/488* (2013.01); *A61B 6/505* (2013.01); *A61B 6/5217* (2013.01)

(58) Field of Classification Search
　　CPC ....... A61B 6/5205; A61B 6/482; A61B 6/488; A61B 6/505; A61B 6/5217; A61B 6/5235
　　See application file for complete search history.

(56) References Cited

U.S. PATENT DOCUMENTS

2013/0022170 A1* 1/2013 Cho ........................ A61B 6/545
　　　　　　　　　　　　　　　　　　　378/62
2020/0077036 A1* 3/2020 Koeda .................. H04N 5/3205

FOREIGN PATENT DOCUMENTS

JP　　　　2008125691 A　*　6/2008
JP　　　　2020031961 A　　3/2020

* cited by examiner

*Primary Examiner* — Casey Bryant
(74) *Attorney, Agent, or Firm* — Canon U.S.A., Inc. IP Division

(57)　　　　　ABSTRACT

An image processing apparatus includes an image obtaining unit configured to obtain a first radiographic image and a second radiographic image, the first radiographic image being obtained by irradiating a subject with radiation of a first energy, the second radiographic image being obtained after the first radiographic image by irradiating the subject with radiation of a second energy different from the first energy, an estimation unit configured to estimate information about an afterimage of the first radiographic image in the second radiographic image based on information about a soft tissue region of the subject in the first radiographic image and the second radiographic image, and a correction unit configured to correct the second radiographic image using the information about the afterimage.

17 Claims, 5 Drawing Sheets

FIG.5A
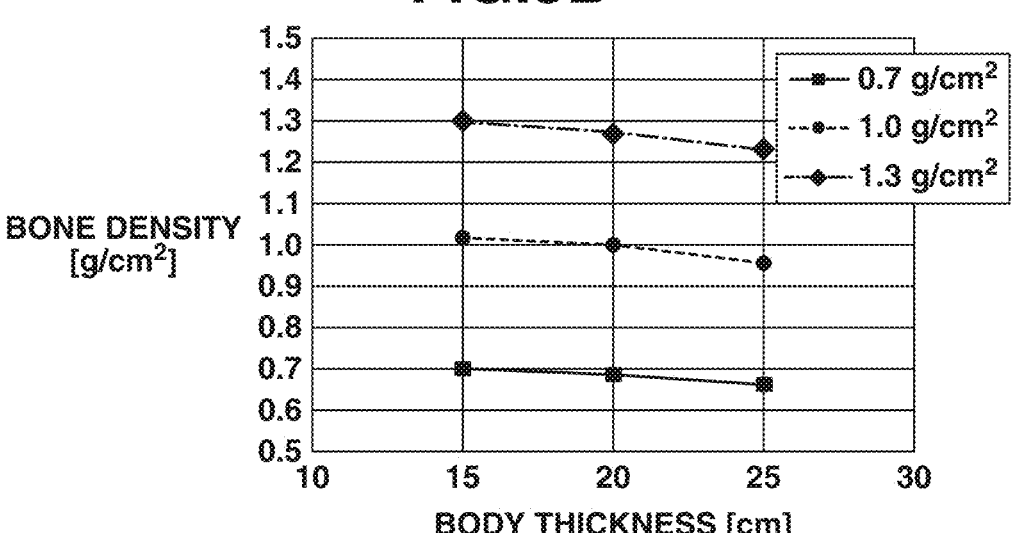
FIG.5B
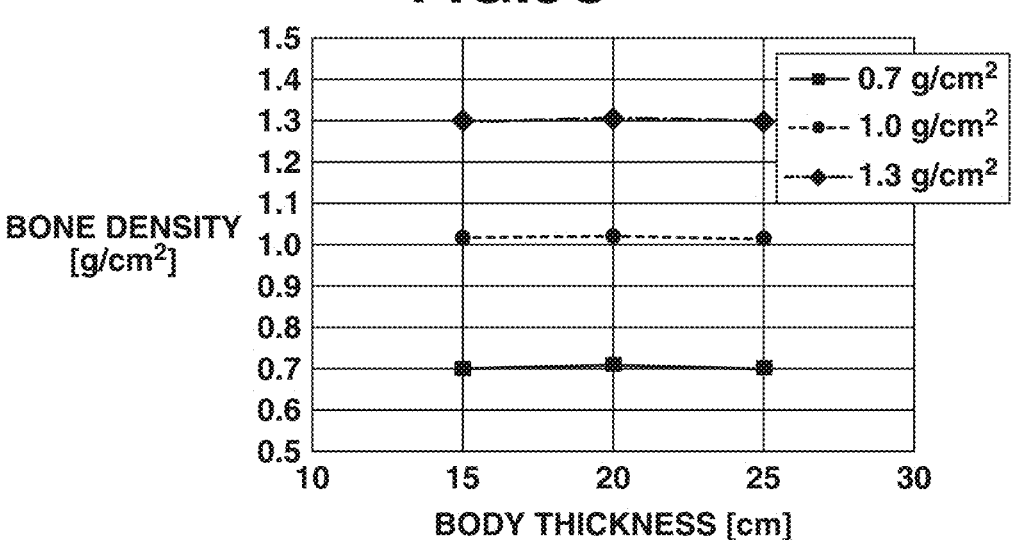
FIG.5C

IMAGE PROCESSING APPARATUS, RADIOGRAPHIC IMAGING SYSTEM, IMAGE PROCESSING METHOD, AND STORAGE MEDIUM

BACKGROUND OF THE DISCLOSURE

Field of the Disclosure

The present disclosure relates to an image processing apparatus, a radiographic imaging system, an image processing method, and a storage medium.

Description of the Related Art

A radiographic imaging apparatus (radiographic imaging system) using a flat panel detector (FPD) is in widespread use as an imaging apparatus for use in medical diagnostic imaging using radiation, such as an X-ray. The FPD is configured to perform digital image processing on captured images. Accordingly, various applications for the FPD have been developed and put to practical use.

Japanese Patent Application Laid-Open No. 2020-31961 discusses a technique in which, in the case of obtaining a plurality of radiographic images by successively irradiating a subject with radiation with different energy distribution, and performing energy subtraction processing thereon, an offset image corresponding to each radiographic image is obtained to correct each radiographic image.

A technique called a dual energy X-ray absorptiometry (DXA) method is known. According to this technique, energy subtraction processing is performed on a plurality of radiographic images obtained by radiographic imaging to generate an image of only bones (bone image) without a soft tissue region of a subject, and a bone density is measured based on the bone image. With acceleration of aging worldwide, the number of patients suffering from osteoporosis has been increasing, and there is an increasing demand for bone density measurement using the DXA method.

The FPD is, for example, a radiation detection apparatus that converts incident radiation into visible light using a phosphor, converts the visible light into electric charges by a photodiode, and detects the electric charges as electric signals. In this case, the photodiode, and a thin-film transistor (TFT) constituting the FPD are formed of, for example, amorphous silicon or indium gallium zinc oxide (IGZO). However, in principle, if the material includes a number of defects, electric charges can be trapped. Accordingly, it is difficult to read all of the electric signals based on the electric charges accumulated in the FPD by performing radiographic imaging once. The electric signals based on the electric charges remaining in the FPD after first radiographic imaging can be read when second and subsequent radiographic imaging is performed. Therefore, an afterimage of a first radiographic image obtained based on the electric signals read from the FPD by the first radiographic imaging can be superimposed on a second radiographic image obtained based on electric signals read from the FPD by second radiographic imaging.

In bone density measurement by the DXA method, it is necessary to measure a bone density independently of a body thickness of a subject. According to the standard for approval of X-ray bone density measurement apparatuses (Apr. 1, 2005, Pharmaceutical and Food Safety Bureau Notification No. 0401050), the variation coefficient of body thickness dependence of a subject is required to be 2% or less. In this case, if the afterimage of the first radiographic image obtained by the first radiographic imaging is superimposed on the second radiographic image obtained by the second radiographic imaging and a bone image is obtained by performing energy subtraction processing on these radiographic images, the bone density, which is measured based on the obtained bone image, is to have high body thickness dependence of the subject.

In this regard, according to the technique discussed in Japanese Patent Application Laid-Open No. 2020-31961, the radiographic images and offset images are not captured simultaneously. Thus, there is an issue that it is difficult to appropriately correct the afterimage of the first radiographic image obtained by the first radiographic imaging in the second radiographic image obtained by the second radiographic imaging.

SUMMARY OF THE DISCLOSURE

The present disclosure has been made in view of the above-described issue and is directed to providing a technique for appropriately correcting an afterimage of a first radiographic image obtained by first radiographic imaging in a second radiographic image obtained by second radiographic imaging.

According to an aspect of the present disclosure, an image processing apparatus includes an image obtaining unit configured to obtain a first radiographic image and a second radiographic image, the first radiographic image being obtained by irradiating a subject with radiation of a first energy, the second radiographic image being obtained after the first radiographic image by irradiating the subject with radiation of a second energy different from the first energy, an estimation unit configured to estimate information about an afterimage of the first radiographic image in the second radiographic image based on information about a soft tissue region of the subject in the first radiographic image and the second radiographic image, and a correction unit configured to correct the second radiographic image using the information about the afterimage.

The present disclosure also includes a radiographic imaging system including the above-described image processing apparatus, an image processing method performed by the above-described image processing apparatus, and a non-transitory computer-readable storage medium storing a program for causing a computer to execute the image processing method.

Further features of the present disclosure will become apparent from the following description of exemplary embodiments with reference to the attached drawings.

BRIEF DESCRIPTION OF THE DRAWINGS

FIGS. 5A to 5C illustrate experimental results indicating effects of the exemplary embodiment of the present disclosure.

DESCRIPTION OF THE EMBODIMENTS

Exemplary embodiments for carrying out the present disclosure will be described below with reference to the drawings. An X-ray is desirably applied as radiation according to the exemplary embodiments of the present disclosure. However, the radiation is no limited to the X-ray. Examples of the radiation according to the exemplary embodiments include not only the X-ray, but also an alpha ($\alpha$)-ray, a beta ($\beta$)-ray, a gamma ($\gamma$)-ray, a particle beam, and a cosmic ray.

Figure 1:
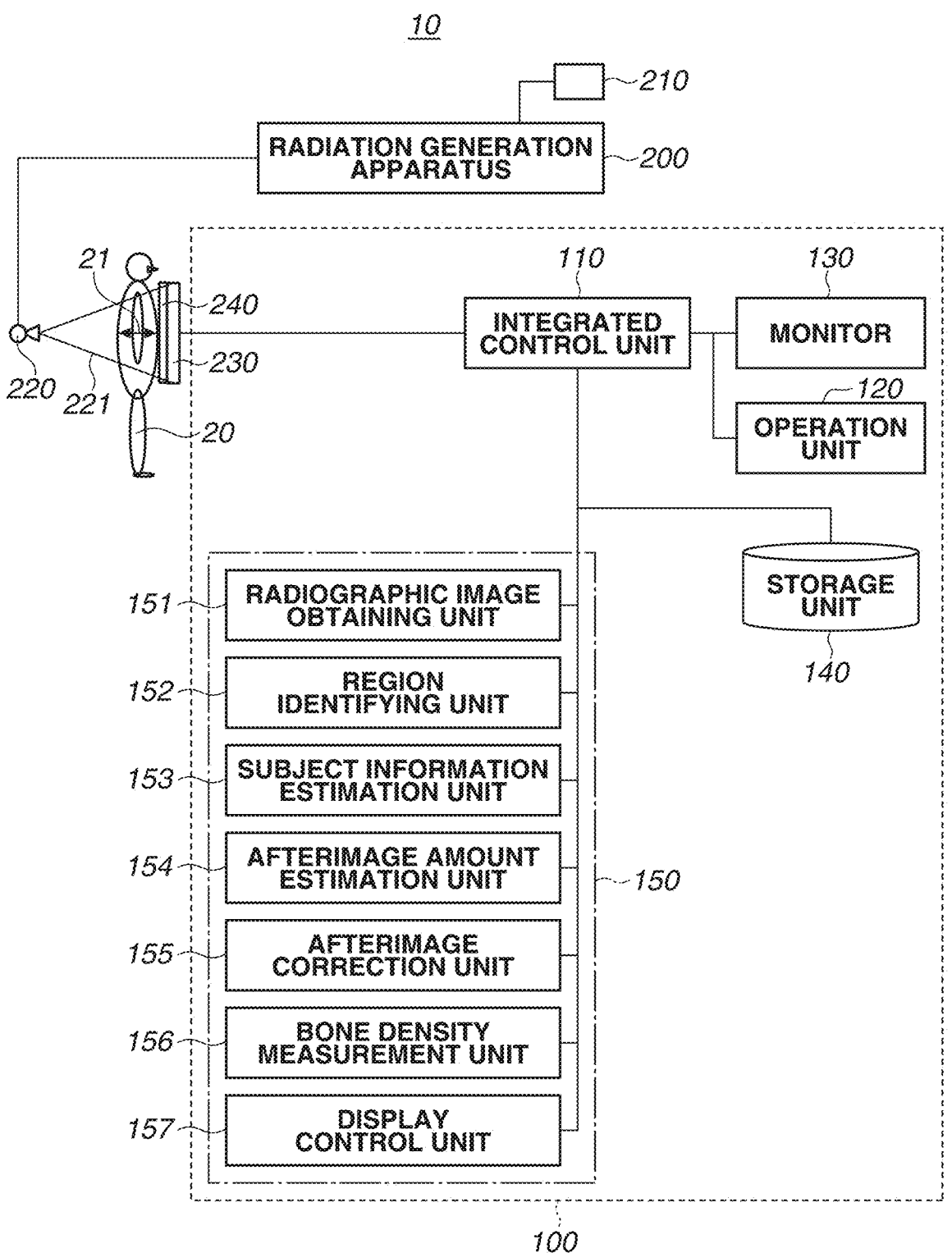
FIG. 1 schematically illustrates an example of a configuration of a radiographic imaging system according to an exemplary embodiment of the present disclosure.

FIG. 1 schematically illustrates an example of a configuration of a radiographic imaging system 10 according to an exemplary embodiment of the present disclosure. In the present exemplary embodiment, the radiographic imaging system 10 is a system for performing radiographic imaging of a subject 20, and may also be referred to as a radiographic imaging apparatus. While the present exemplary embodiment illustrates an example where a human body is applied as the subject 20, the subject according to the present exemplary embodiment is not limited to a human body. For example, a body of an animal other than a human may be applied.

As illustrated in FIG. 1, the radiographic imaging system 10 includes an information processing apparatus 100, a radiation generation apparatus 200, an exposure switch 210, a radiation tube 220, a radiation detection apparatus 230, and a scattered ray removal grid 240.

For example, when the exposure switch 210 is operated by a user, the radiation generation apparatus 200 applies a voltage pulse to the radiation tube 220 to generate radiation 221 from the radiation tube 220. In the example illustrated in FIG. 1, the radiation tube 220 emits the radiation 221 toward the subject 20. FIG. 1 also illustrates a body thickness of the subject 20 as a body thickness 21. A part of the radiation 221 emitted toward the subject 20 passes through the subject 20 and enters the radiation detection apparatus 230 through the scattered ray removal grid 240. The scattered ray removal grid 240 has a function for preventing scattered rays generated on the subject 20 from entering the radiation detection apparatus 230.

The radiation detection apparatus 230 detects the radiation 221 that has passed through the subject 20 as an electric signal (image signal). As the radiation detection apparatus 230, for example, a flat panel detector (FPD) as described above can be desirably applied. Specifically, the radiation detection apparatus 230 includes a radiation detection unit in which pixels, each configured to output a signal (electric charge) corresponding to the incident radiation 221, are arranged in an array (two-dimensional region). For example, each pixel in the radiation detection unit of the radiation detection apparatus 230 converts the incident radiation 221 into visible light using a phosphor, converts the visible light into electric charges by a photodiode, and detects the electric charges as electric signals. Further, the radiation detection apparatus 230 transmits the detected electric signals to the information processing apparatus 100. In this case, for example, a driving unit (not illustrated) of the radiation detection apparatus 230 outputs the detected electric signals to an integrated control unit 110 according to an instruction from the integrated control unit 110 of the information processing apparatus 100.

The information processing apparatus 100 processes various kinds of information including electric signals (image signals) obtained by the radiation detection apparatus 230 by capturing an image of the subject 20 using the radiation 221. As illustrated in FIG. 1, the information processing apparatus 100 includes the integrated control unit 110, an operation unit 120, a monitor 130, a storage unit 140, and an image processing unit 150.

The integrated control unit 110 includes one or more processors (not illustrated), and executes programs stored in the storage unit 140 to thereby implement various kinds of control and various kinds of processing for the information processing apparatus 100.

The operation unit 120 inputs information input by a user operation to, for example, the integrated control unit 110 and the monitor 130. For example, the operation unit 120 is capable of inputting instructions for the image processing unit 150 and the radiation detection apparatus 230 to the integrated control unit 110. For example, the operation unit 120 receives input of an instruction for the radiation detection apparatus 230 via a user interface (not illustrated).

The monitor 130 (display unit) displays various images, including radiographic images obtained by the image processing unit 150, and various kinds of information obtained by performing control or processing by the integrated control unit 110.

The storage unit 140 stores programs, information, and the like to be used by the integrated control unit 110 to implement various kinds of control and various kinds of processing. The storage unit 140 stores information obtained by the integrated control unit 110 performing various kinds of control and various kinds of processing, and radiographic images, information, and the like obtained by the image processing unit 150. The storage unit 140 includes, for example, a read-only memory (ROM) and a random access memory (RAM).

The image processing unit 150 obtains a radiographic image by processing the electric signal (image signal) output from the radiation detection apparatus 230 via the integrated control unit 110, and performs various kinds of processing on the obtained radiographic image. In the present exemplary embodiment, the image processing unit 150 may also be referred to as an image processing apparatus. As illustrated in FIG. 1, the image processing unit 150 includes functional units such as a radiographic image obtaining unit 151, a region identifying unit 152, a subject information estimation unit 153, an afterimage amount estimation unit 154, an afterimage correction unit 155, a bone density measurement unit 156, and a display control unit 157.

The functional units 151 to 157 of the image processing unit 150 may be implemented by one or more processors included in the integrated control unit 110 executing programs read from the storage unit 140. The functional units 151 to 157 of the image processing unit 150 may also be implemented by one or more processors included in the image processing unit 150 executing programs read from the storage unit 140. In this case, each of the processors of the integrated control unit 110 and the image processing unit 150 may be composed of, for example, a central processing unit (CPU). Each of the functional units 151 to 157 of the image processing unit 150 may be composed of an integrated circuit or the like as long as similar functions can be achieved. An internal configuration of the information processing apparatus 100 may include a graphics control unit such as a graphics processing unit (GPU), a communication unit such as a network card, and an input/output control unit such as a keyboard, a display, and a touch panel.

In the present exemplary embodiment, for example, when the exposure switch 210 is operated by the user, the radiation generation apparatus 200 applies two different voltages (kV switching) to the radiation tube 220 in a short period of time of 0.1 seconds to 1.0 second. At this time, the second applied voltage (e.g., about 140 kV) is higher than the first applied voltage (e.g., about 80 kV). Thus, the low-energy radiation 221 obtained by applying a low voltage is emitted toward the subject 20 and the high-energy radiation 221 obtained by applying a high voltage is emitted toward the subject 20 sequentially from the radiation tube 220 at predetermined time intervals. In other words, in the present exemplary embodiment, the subject 20 is irradiated with the radiation 221 of a low energy (first energy) and the radiation 221 of a high energy (second energy) different from the low energy (higher than the low energy) sequentially at predetermined time intervals. The radiation detection apparatus 230 sequentially performs detection of the low-energy radiation 221 that has passed through the subject 20 as an electric signal (image signal) and detection of the high-energy radiation 221 that has passed through the subject 20 as an electric signal (image signal) at the predetermined time intervals. Thus, first radiographic imaging of the subject 20 using the low-energy radiation 221 and second radiographic imaging of the subject 20 using the high-energy radiation 221 are performed. Then, the integrated control unit 110 sequentially receives the electric signal (image signal) obtained by the first radiographic imaging and the electric signal (image signal) obtained by the second radiographic imaging from the radiation detection apparatus 230.

First, the radiographic image obtaining unit 151 sequentially obtains the electric signal (image signal) obtained by the first radiographic imaging and the electric signal (image signal) obtained by the second radiographic imaging from the radiation detection apparatus 230. The radiographic image obtaining unit 151 is an image obtaining unit that obtains a first radiographic image by processing the electric signal (image signal) obtained by the first radiographic imaging, and obtains a second radiographic image by processing the electric signal (image signal) obtained by the second radiographic imaging. In the present exemplary embodiment, the first radiographic image corresponds to a low-energy radiographic image $I_L$ obtained by performing the first radiographic imaging in which the subject 20 is irradiated with the radiation 221 of the low energy (first energy). The second radiographic image corresponds to a high-energy radiographic image $I_H$ obtained after the first radiographic image described above, by performing the second radiographic imaging in which the subject 20 is irradiated with the radiation 221 of the high energy (second energy), which is higher than the low energy described above. The low-energy radiographic image $I_L$ that is the first radiographic image obtained by the radiographic image obtaining unit 151 includes data in which a signal value (pixel value) of the electric signal (image signal) obtained by the first radiographic imaging is simply associated with positional information. Similarly, the high-energy radiographic image $I_H$ that is the second radiographic image obtained by the radiographic image obtaining unit 151 includes data in which a signal value (pixel value) of the electric signal (image signal) obtained by the second radiographic imaging is simply associated with positional information.

The region identifying unit 152 is an identifying unit that identifies a soft tissue region, which is a portion of soft tissue (muscle, viscera, fat, etc.) other than bones of the subject 20, from the low-energy radiographic image $I_L$ and the high-energy radiographic image $I_H$ obtained by the radiographic image obtaining unit 151. In the present exemplary embodiment, the low-energy radiographic image $I_L$ and the high-energy radiographic image $I_H$ are obtained by irradiating the subject 20 with the radiation 221 of two different energies. This configuration makes it possible to separately obtain a bone image and a soft tissue image of the subject 20 by performing energy subtraction processing on the low-energy radiographic image $I_L$ and the high-energy radiographic image $I_H$. More specifically, since the bone image and the soft tissue image of the subject 20 can be separately obtained, the soft tissue region of the subject 20 can be easily identified. In the present exemplary embodiment, however, identifying the soft tissue region of the subject 20 by the region identifying unit 152 need not necessarily use the bone image and the soft tissue image obtained as a result of performing image processing on the low-energy radiographic image $I_L$ and the high-energy radiographic image $I_H$. For example, a region of interest (ROI) designated by the user on an image displayed on a display screen, on which the low-energy radiographic image $I_L$, the high-energy radiographic image $I_H$, or a processed image obtained by processing the low-energy radiographic image $I_L$ or the high-energy radiographic image $I_H$ is displayed, may be identified as the soft tissue region of the subject 20. In this case, a graphical user interface (GUI) may be desirably used as the display screen. If a large number of radiographic images of the subject 20 can be prepared in advance, the soft tissue region of the subject 20 may be identified using, for example, semantic segmentation by machine learning.

The subject information estimation unit 153 estimates information about the soft tissue region of the subject 20 identified by the region identifying unit 152 using the low-energy radiographic image $I_L$ and the high-energy radiographic image $I_H$ obtained by the radiographic image obtaining unit 151. Specifically, the subject information estimation unit 153 performs a logarithmic transformation on the low-energy radiographic image $I_L$ and the high-energy radiographic image $I_H$ to thereby estimate information indicating an amount that is proportional to the body thickness 21 of the subject 20 in the soft tissue region as the information about the soft tissue region of the subject 20.

The afterimage amount estimation unit 154 estimates an afterimage amount of the low-energy radiographic image $I_L$, which is the first radiographic image, in the high-energy radiographic image $I_H$, which is the second radiographic image, based on the information about the soft tissue region of the subject 20 estimated by the subject information estimation unit 153. In the exemplary embodiment of the present disclosure, the "afterimage amount" of the first radiographic image in the second radiographic image is an example of "information about an afterimage". Specifically, the afterimage amount estimation unit 154 obtains information indicating an amount that is independent of the body thickness 21 of the subject 20 by performing division on the information indicating the amount proportional to the body thickness 21 of the subject 20 in the soft tissue region in each of the low-energy radiographic image $I_L$ and the high-energy radiographic image $I_H$. As described below, in a case where an effect of beam hardening is small, the amount is almost independent of the body thickness 21 of the subject 20. However, if the amount is affected by the afterimage, the amount is to have dependence on the body thickness of the subject 20. Accordingly, an amount of the afterimage to be removed is adjusted so that the dependence of the amount on the body thickness of the subject 20 is reduced, thereby the afterimage amount estimation unit 154 can estimate the afterimage amount of the low-energy radiographic image $I_L$ in the high-energy radiographic image $I_H$. In the present exemplary embodiment, the subject information estimation unit 153 and the afterimage amount estimation unit 154 constitute an estimation unit.

The afterimage correction unit 155 is a correction unit that corrects the high-energy radiographic image $I_H$, which is the second radiographic image, using the afterimage amount estimated by the afterimage amount estimation unit 154. Specifically, the afterimage correction unit 155 performs afterimage correction by subtracting the afterimage amount estimated by the afterimage amount estimation unit 154 from the high-energy radiographic image $I_H$.

In the present exemplary embodiment, the low-energy radiographic image $I_L$ is obtained first as the first radiographic image, so that the afterimage amount of the low-energy radiographic image $I_L$ is superimposed on the high-energy radiographic image $I_H$ obtained by the subsequent second radiographic imaging. If some of the electric signals accumulated in the radiation detection apparatus 230 by the first radiographic imaging are not read, and the unread electric signals are read together with the electric signals accumulated in the radiation detection apparatus 230 by the second radiographic imaging, these electric signals are superimposed on the second radiographic image as the afterimage amount. In the present exemplary embodiment, the first radiographic image obtained by the first radiographic imaging is used as the low-energy radiographic image $I_L$, and the second radiographic image obtained by the subsequent second radiographic imaging is used as the high-energy radiographic image $I_H$. However, the configuration according to the exemplary embodiment of the present disclosure is not limited to this configuration. The exemplary embodiment of the present disclosure can also be applied to a configuration in which the first radiographic image obtained by the first radiographic imaging is used as the high-energy radiographic image $I_H$, and the second radiographic image obtained by the subsequent second radiographic imaging is used as the low-energy radiographic image $I_L$. In this case, however, the configuration in which the low-energy radiographic image $I_L$ is obtained by the first radiographic imaging and the high-energy radiographic image $I_H$ is obtained by the subsequent second radiographic imaging may be more desirable because the low-energy radiation 221 is used in the first radiographic imaging, which leads to a reduction in the afterimage amount described above.

The bone density measurement unit 156 first obtains the bone image of the subject 20 by performing energy subtraction processing on the low-energy radiographic image $I_L$, which is the first radiographic image, and the high-energy radiographic image $I_H$, which is the second radiographic image on which the afterimage correction has been performed by the afterimage correction unit 155. The bone image of the subject 20 is an image including the bones of the subject 20 that are different from the soft tissue in the soft tissue region identified by the region identifying unit 152. The bone density measurement unit 156 is a measurement unit that measures the bone density of a predetermined bone of the subject 20 using the obtained bone image. Specifically, the bone density measurement unit 156 measures the bone density of the predetermined bone using a pixel value for the predetermined bone in the obtained bone image. The bone density measurement unit 156 is configured to measure bone densities of a plurality of bones with regard to a plurality of body thicknesses 21 of the subject 20.

The display control unit 157 is a display control unit that causes the monitor 130, which is the display unit, to display the bone density measured by the bone density measurement unit 156 via the integrated control unit 110. In the present exemplary embodiment, the display control unit 157 causes the monitor 130 to also display the low-energy radiographic image $I_L$, which is the first radiographic image, the high-energy radiographic image $I_H$, which is the second radiographic image, or a processed image obtained by performing energy subtraction processing on these images.

Figure 2:
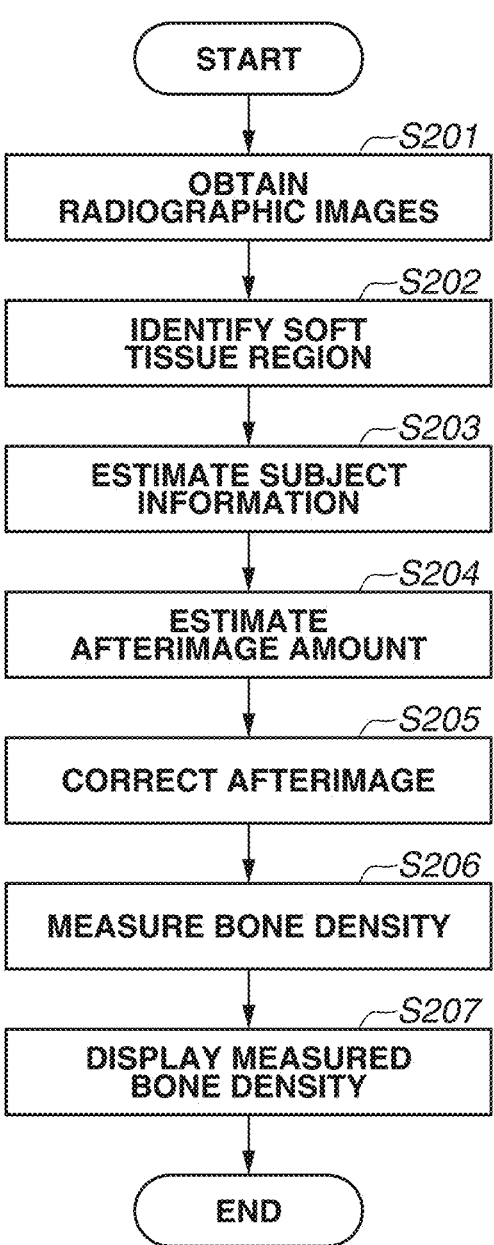
FIG. 2 is a flowchart illustrating an example of a processing procedure of an image processing method for an image processing unit (image processing apparatus) according to the exemplary embodiment of the present disclosure.

FIG. 2 is a flowchart illustrating an example of a processing procedure of an image processing method for the image processing unit 150 (image processing apparatus) according to the exemplary embodiment of the present disclosure. In the present exemplary embodiment, the low-energy radiographic image $I_L$ and the high-energy radiographic image $I_H$ each obtained by performing radiographic imaging of the subject 20 are divided and standardized using a radiographic image obtained under the same imaging conditions as those for the radiographic images $I_L$ and $I_H$ without placing the subject 20. The division and standardization is not essential, but may be desirably performed to facilitate calculations.

<Step S201>

After the processing in the flowchart illustrated in FIG. 2 is started, the processing proceeds to step S201.

In step S201, first, the radiographic image obtaining unit 151 sequentially obtains the electric signal (image signal) obtained by the first radiographic imaging and the electric signal (image signal) obtained by the second radiographic imaging from the radiation detection apparatus 230. Next, the radiographic image obtaining unit 151 processes the electric signal (image signal) obtained by the first radiographic imaging, thereby obtaining the low-energy radiographic image $I_L$, which is the first radiographic image. Then, the radiographic image obtaining unit 151 processes the electric signal (image signal) obtained by the second radiographic imaging, thereby obtaining the high-energy radiographic image $I_H$, which is the second radiographic image.

<Step S202>

After the processing of step S201 ends, the processing proceeds to step S202.

In step S202, the region identifying unit 152 identifies the soft tissue region, which is a portion of soft tissue (muscle, viscera, fat, etc.) other than bones of the subject 20, from the low-energy radiographic image $I_L$ and the high-energy radiographic image $I_H$ obtained in step S201. An example of detailed processing of step S202 will be described below.

FIGS. 3A to 3D illustrate examples of various images to be processed by the image processing unit 150 (image processing apparatus) according to the exemplary embodiment of the present disclosure.

Figure 3A:
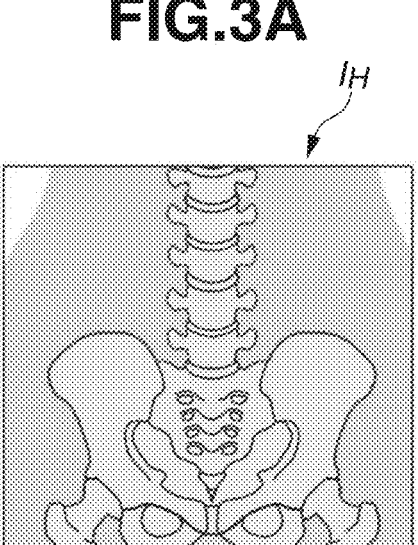
FIGS. 3A to 3D illustrate examples of various images to be processed by the image processing unit (image processing apparatus) according to the exemplary embodiment of the present disclosure.
Figure 3B:
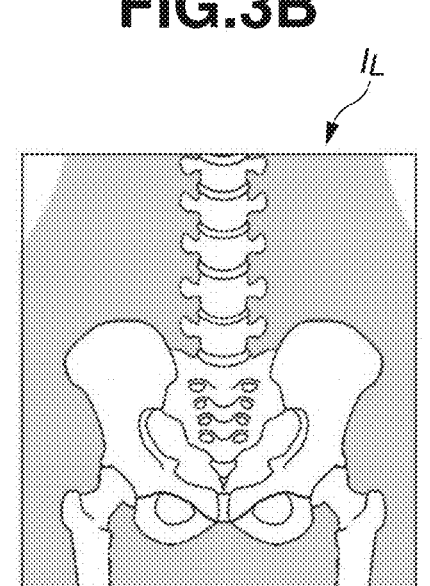

In step S202, the region identifying unit 152 first generates a bone image $d_B$ illustrated in FIG. 3C by Formula (1) described below using the high-energy radiographic image $I_H$ illustrated in FIG. 3A and the low-energy radiographic image $I_L$ illustrated in FIG. 3B that are obtained in step S201.

$$d_B(x, y) = \frac{\mu_{HA}\ln I_L(x, y) - \mu_{LA}\ln I_H(x, y)}{\mu_{HB}\mu_{LA} - \mu_{LB}\mu_{HA}} \tag{1}$$

In Formula (1), "$\mu_{HA}$" represents a mass attenuation coefficient for the soft tissue of the subject 20 under the high energy (second energy), and "$\mu_{HB}$" represents a mass attenuation coefficient for the bones of the subject 20 under the high energy. Further, in Formula (1), "$\mu_{LA}$" represents a mass attenuation coefficient for the soft tissue of the subject 20 under the low energy (first energy), and "$\mu_{L_B}$" represents a mass attenuation coefficient for the bones of the subject 20 in the low energy. In Formula (1), "x" represents a pixel position in a lateral direction of the image, and "y" represents a pixel position in a longitudinal direction of the image. Further, the bone image $d_B$ represented by Formula (1) is expressed in units of surface density [g/cm²].

Figure 3C:
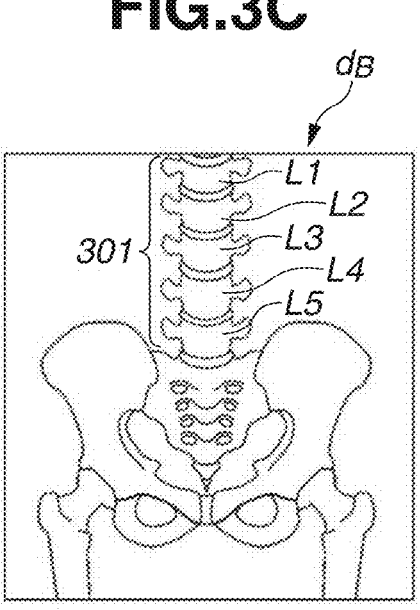

Portions of a lumbar spine 301 of the subject 20 included in the bone image $d_B$ illustrated in FIG. 3C are indicated by reference numerals L1, L2, L3, L4, and L5 from the top, and each of the portions is a main portion on which bone density measurement is performed by a dual energy X-ray absorptiometry (DXA) method. The lumbar spine 301 is a portion where a change in bone density is prominent, and is suitably used for diagnosis of osteoporosis and checking the efficacy of a medication. Another example of the main portion on which the bone density measurement is performed by the DXA method is a thigh bone 303 illustrated in FIG. 3D. A patient with a fracture in the thigh bone 303 may need an invasive treatment, such as implant, and may be confined to bed, which leads to a decrease in healthy life expectancy. For this reason, the thigh bone 303 is a portion that is useful for clinical practice. In the exemplary embodiment of the present disclosure, both the lumbar spine 301 and the thigh bone 303 can be applied as portions on which the bone density measurement is performed. The same method can be applied to the lumbar spine 301 and the thigh bone 303, and thus a case where the lumbar spine 301 is applied will be described below.

Figure 3D:
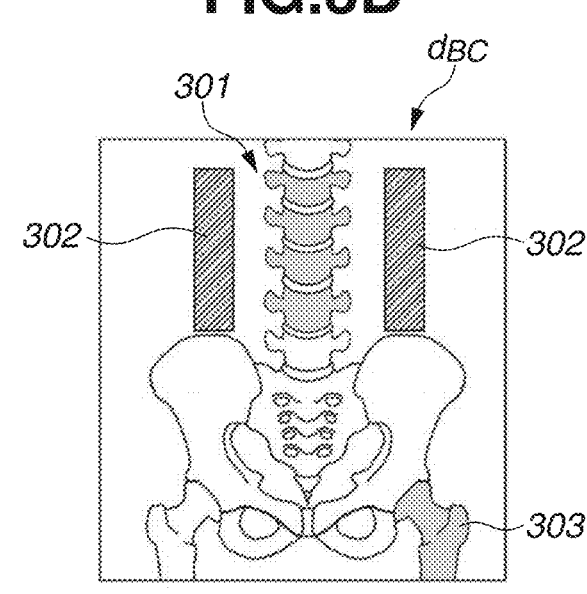

The region identifying unit 152 identifies, for example, an ROI 302 illustrated in FIG. 3D as the soft tissue region composed of soft tissue located at a predetermined distance from the lumbar spine 301 on which the bone density measurement is performed. The position and size of the ROI 302, which is the soft tissue region, do not vary greatly depending on a person who is the subject 20, and thus predetermined values may be set as the position and size of the ROI 302.

The region identifying unit 152 extracts, for example, a region corresponding to the lumbar spine 301 by performing image processing of segmenting the bone image $d_B$ illustrated in FIG. 3C. In this case, for example, a method of designating a peripheral region of the lumbar spine 301 and performing threshold processing is well known as a segmentation processing method. Otsu's method or the like may be used as the threshold processing in this case. The region corresponding to the lumbar spine 301 may also be extracted by known techniques, such as k-means clustering, snakes method, a region growing method, an edge detection method, and a graph-cut method. Further, if a large number of radiographic images of the subject 20 can be obtained, the region corresponding to the lumbar spine 301 may be extracted using segmentation processing by machine learning.

In the present exemplary embodiment, the bone image de illustrated in FIG. 3C is used to facilitate identifying of the soft tissue region. However, the configuration according to the exemplary embodiment of the present disclosure is not limited to this configuration. For example, in the exemplary embodiment of the present disclosure, the ROI 302, which is the soft tissue region composed of the soft tissue of the subject 20, may be identified by using the above-described known techniques on the high-energy radiographic image $I_H$ or the low-energy radiographic image $I_L$. Further, the ROI 302, which is the soft tissue region composed of the soft tissue of the subject 20, may be directly identified by using the above-described known techniques without extracting a bone region that is a portion on which the bone density measurement is performed. The shape of the ROI 302 is not limited to a rectangular shape, but instead may be any shape, as long as the ROI 302 does not include the bones of the subject 20.

In the present exemplary embodiment described above, the region identifying unit 152 identifies the soft tissue region of the subject 20 by performing image processing on the low-energy radiographic image $I_L$, the high-energy radiographic image $I_H$, or the processed image obtained by performing the energy subtraction processing on the low-energy radiographic image $I_L$ and the high-energy radiographic image $I_H$. However, the present disclosure is not limited to the present exemplary embodiment described above. For example, the region identifying unit 152 may identify, as the soft tissue region, the ROI 302 designated by the user on an image displayed on a display screen, on which the low-energy radiographic image $I_L$, the high-energy radiographic image $I_H$, or the processed image obtained by performing the energy subtraction processing on the low-energy radiographic image $I_L$ or the high-energy radiographic image $I_H$ is displayed. A configuration in which the user designates the ROI 302 on the display screen (display screen using a GUI) will be described below with reference to FIG. 4.

Figure 4:
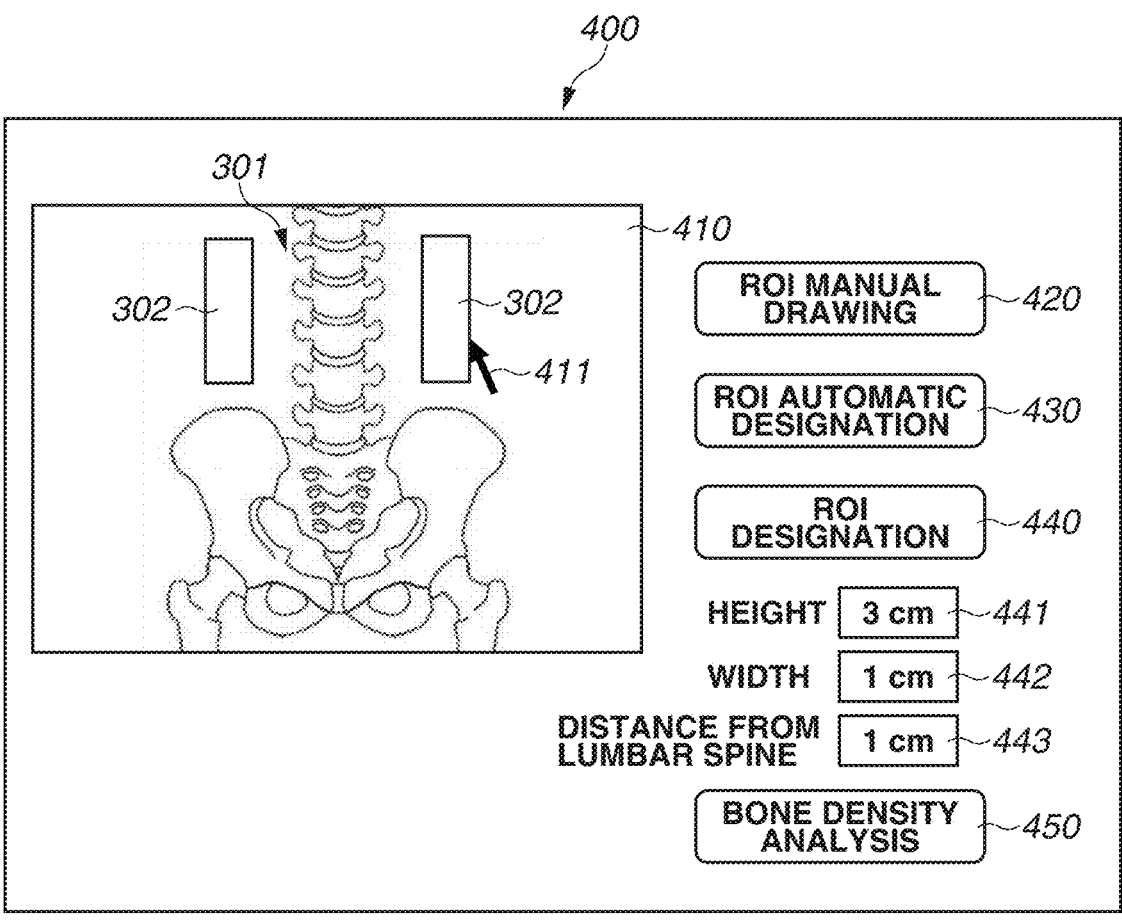
FIG. 4 illustrates an example of a configuration in which a user designates a region of interest (ROI) as a soft tissue region of a subject on a display screen according to the exemplary embodiment of the present disclosure.

FIG. 4 illustrates an example of a configuration in which the user designates the ROI 302 as the soft tissue region of the subject 20 on a display screen 400 according to the exemplary embodiment of the present disclosure. The display screen 400 illustrated in FIG. 4 is a GUI screen to be displayed on the monitor 130 illustrated in FIG. 1, and can be operated using the operation unit 120. The display screen 400 includes an image display region 410, an ROI manual drawing button 420, an ROI automatic designation button 430, an ROI designation button 440, a height designation section 441, a width designation section 442, a distance designation section 443, and a bone density analysis button 450. On the image display region 410 of the display screen 400, for example, the low-energy radiographic image $I_L$, the high-energy radiographic image $I_H$, or the bone image de obtained as a result of performing the energy subtraction processing on the low-energy radiographic image $I_L$ and the high-energy radiographic image $I_H$ is displayed. The ROI manual drawing button 420 is, for example, a button to be operated when the user designates the ROI 302 by manually drawing the ROI 302 using a pointer 411. As described above in the present exemplary embodiment, the ROI automatic designation button 430 is a button to be operated when the user wants the ROI 302 as the soft tissue region of the subject 20 to be automatically designated by performing image processing on the image displayed on the image display region 410. The ROI designation button 440 is a button to be operated when the user designates the ROI 302 by setting values in the height designation section 441 to designate the height of the ROI 302, the width designation section 442 to designate the width of the ROI 302, and the distance designation section 443 to designate a distance of the ROI 302 from the lumbar spine 301. The bone density analysis button 450 is a button to be operated when the bone density of the lumbar spine 301 of the subject 20 is analyzed. The position of the ROI 302 may be finely adjusted by a combination of operations of the ROI manual drawing button 420, the ROI automatic designation button 430, and the ROI designation button 440 (associated with the height designation section 441, the width designation section 442, and the distance designation section 443).

<Step S203>

After the processing of step S202 ends, the processing proceeds to step S203.

In step S203, the subject information estimation unit 153 estimates information about the soft tissue region of the subject 20 identified in step S202 using the low-energy radiographic image $I_L$ and the high-energy radiographic image $I_H$ obtained in step S201. Specifically, the subject information estimation unit 153 performs a logarithmic transformation on the low-energy radiographic image $I_L$ and the high-energy radiographic image $I_H$ to thereby estimate information indicating an amount that is proportional to the body thickness 21 of the subject 20 in the soft tissue region as the information about the soft tissue region of the subject 20. More specifically, the subject information estimation unit 153 estimates the information indicating the amount that is proportional to the body thickness 21 of the subject 20 in the soft tissue region identified in step S202 using the high-energy radiographic image $I_H$ and the low-energy radiographic image $I_L$ by Formulas (2) and (3) described below. In Formulas (2) and (3), the body thickness 21 of the subject 20 illustrated in FIG. 1 is represented by $d_A(x, y)$ in an xy coordinate system. Specifically, the left-hand side of Formula (2) described below corresponds to information indicating the amount that is proportional to the body thickness $d_A(x, y)$ of the subject 20 in the soft tissue region in the high-energy radiographic image $I_H$. The left-hand side of the Formula (3) described below corresponds to information indicating the amount proportional to the body thickness $d_A(x, y)$ of the subject 20 in the soft tissue region in the low-energy radiographic image $I_L$.

$$-\ln I_H(x, y) = \mu_{HA} d_A(x, y) \tag{2}$$

$$-\ln I_L(x, y) = \mu_{LA} d_A(x, y) \tag{3}$$

Since it is obvious that the soft tissue region of the subject 20 consists only of the soft tissue, simple calculations as Formulas (2) and (3) described above can be established. In practice, the spectrum of the radiation 221 has a broad width, and thus a single color approximation as described above can be established with certain accuracy although there may be an effect of beam hardening. The radiation detection apparatus 230 illustrated in FIG. 1 is in direct contact with the scattered ray removal grid 240, which indicates that scattered rays are sufficiently removed. Accordingly, it is considered that an effect of scattered rays is small. In practice, it is desirable to set a grating ratio of the scattered ray removal grid 240 to "10" or more for a diagnosis with high accuracy, such as bone density measurement by the DXA method. It is more desirable to use a crossed grid that is two parallel grids perpendicularly combined to form a grid-pattern as the scattered ray removal grid 240. In this case, the crossed grid is capable of removing scattered rays in vertical and horizontal directions. Thus, the crossed grid can isotropically remove scattered rays, and has an absolute removal capability of scattered rays.

<Step S204>

After the processing of step S203 ends, the processing proceeds to step S204.

In step S204, the afterimage amount estimation unit 154 estimates the afterimage amount of the low-energy radiographic image $I_L$ in the high-energy radiographic image $I_H$ based on the information about the soft tissue region of the subject 20 estimated in step S203. Specifically, the afterimage amount estimation unit 154 estimates the afterimage amount using the information indicating the amount that is proportional to the body thickness $d_A(x, y)$ of the subject 20 in the low-energy radiographic image $I_L$ and the information indicating the amount that is proportional to the body thickness $d_A(x, y)$ of the subject 20 in the high-energy radiographic image $I_H$. The processing of step S204 will be described in more detail below.

The afterimage amount estimation unit 154 estimates an afterimage amount coefficient α as the afterimage amount of the low-energy radiographic image $I_L$ in the high-energy radiographic image $I_H$ by the following procedure. First, the afterimage amount estimation unit 154 divides the above-described Formula (3) by the above-described Formula (2), thereby calculating a ratio (logarithmic ratio) γ represented by Formula (4) below.

$$\frac{\ln I_L}{\ln I_H} = \frac{\mu_{LA}}{\mu_{HA}} = \gamma \tag{4}$$

The ratio γ represented by Formula (4) is a ratio of attenuation coefficients, and represents an amount that is approximately independent of the body thickness $d_A$ of the subject 20.

On the other hand, if the afterimage of the low-energy radiographic image $I_L$ is superimposed on the high-energy radiographic image $I_H$ at the ratio of the afterimage amount coefficient α, Formula (5) described below holds, and the ratio (logarithmic ratio) γ between the high-energy radiographic image $I_H$ and the low-energy radiographic image $I_L$ is dependent on the body thickness $d_A$.

$$\frac{\ln I_L}{\ln(I_H + \alpha I_L)} = \frac{\mu_{LA} d_A}{\ln\left(e^{-\mu_{HA} d_A} + \alpha e^{-\mu_{LA} d_A}\right)} \tag{5}$$

For example, the ratio (logarithmic ratio) γ can be obtained from the logarithmic ratio represented by Formula (4) described above in a state where an imaging interval between the low-energy radiographic image $I_L$ and the high-energy radiographic image $I_H$ is set to an extremely large value (several tens of seconds) in advance and where the afterimage has almost disappeared. In this case, a first obtaining time interval (several tens of seconds) between the low-energy radiographic image $I_L$ and the high-energy radiographic image $I_H$ used to estimate the afterimage amount in step S204 is larger than a second obtaining time interval (0.1 seconds to 1.0 second) between the low-energy radiographic image $I_L$ and the high-energy radiographic image $I_H$ used to measure the bone density.

In the case of capturing images to obtain the ratio (logarithmic ratio) γ, image capturing without applying the radiation 221 may be performed several times during a period between capturing of the low-energy radiographic image $I_L$ and capturing of the high-energy radiographic image $I_H$. Instead of actually performing the image capturing, reading of electric signals from the radiation detection apparatus 230 may be performed a plurality of times during an interval between obtaining times of the low-energy radiographic image $I_L$ and the high-energy radiographic image $I_H$. In this case, the reading of electric signals from the radiation detection apparatus 230 is performed a plurality of times during the interval between the obtaining times of the low-energy radiographic image $I_L$ and the high-energy radiographic image $I_H$ used to estimate the afterimage amount in step S204.

The above-described processing makes it possible to effectively eliminate electric signals based on electric charges trapped in defects of amorphous silicon or the like of the radiation detection apparatus 230, which leads to a reduction in effects of the afterimage.

The afterimage amount can be estimated, as expressed by Formula (6) described below, by determining the afterimage amount coefficient $\alpha$ such that the logarithmic ratio of the low-energy radiographic image $I_L$ and the high-energy radiographic image $I_H$, from which $\alpha I_L$ is subtracted, obtained at an actual imaging interval (0.1 seconds to 1 second) is $\gamma$.

$$\frac{\ln I_L}{\ln(I_H - \alpha I_L)} = \gamma \qquad (6)$$

In some cases, it may be difficult to measure the ratio (logarithmic ratio) $\gamma$ in advance in the subject 20 that is an actual human body. It is difficult for a human body to stay still for several tens of seconds as described above, and radiographic images obtained in such a state cannot be used for diagnosis, which results in ineffective exposure to the radiation 221. In this case, for example, the ratio (logarithmic ratio) $\gamma$ may be obtained using a phantom, which is a model of the subject 20 and is made of a material such as polyurethane or acrylic that is similar to a soft tissue of a human.

In the case of using the phantom made of the material such as polyurethane or acrylic, which is similar to the soft tissue of a human, the afterimage amount coefficient $\alpha$ can be estimated in advance without using the ratio (logarithmic ratio) $\gamma$. For example, a low-energy radiographic image $I_{L1}$ and a high-energy radiographic image $I_{H1}$ are captured using a phantom made of thin polyurethane, and the low-energy radiographic image $I_{L1}$ and the high-energy radiographic image $I_{H1}$ are captured using a phantom made of thick polyurethane. In this case, the afterimage amount coefficient $\alpha$ may be determined to satisfy Formula (7) described below. If the afterimage amount coefficient $\alpha$ is appropriate, the left-hand side and the right-hand side of Formula (7) described below represent the ratio (logarithmic ratio) $\gamma$, and indicate an amount having no dependence on the body thickness of the subject 20.

$$\frac{\ln I_{L1}}{\ln(I_{H1} - \alpha I_{L1})} = \frac{\ln I_{L2}}{\ln(I_{H2} - \alpha I_{L2})} \qquad (7)$$

Since Formula (7) described above is a non-linear equation, the afterimage amount coefficient $\alpha$ may be obtained using a solver such as non-linear least squares. Three or more phantoms made of polyurethane each with a different thickness may also be used. In such a case, the afterimage amount coefficient $\alpha$ can be obtained with higher accuracy.
<Step S205>

After the processing of step S204 ends, the processing proceeds to step S205.

In step S205, the afterimage correction unit 155 corrects the high-energy radiographic image $I_H$, which is the second radiographic image, using the afterimage amount estimated in step S204. Specifically, the afterimage correction unit 155 obtains a high-energy radiographic image $I_{Hc}$ on which the afterimage correction has been performed based on Formula (8) using the high-energy radiographic image $I_H$, the low-energy radiographic image $I_L$, and the afterimage amount coefficient $\alpha$ estimated in step S204.

$$I_{HC} = (I_H - \alpha I_L) \qquad (8)$$

<Step S206>

After the processing of step S205 ends, the processing proceeds to step S206.

In step S206, the bone density measurement unit 156 obtains an afterimage-reduced bone image $d_{BC}$ based on Formula (9) described below using the low-energy radiographic image $I_L$ obtained in step S201 and the high-energy radiographic image $I_{Hc}$, on which the afterimage correction has been performed, obtained in step S205.

$$d_{BC}(x, y) = \frac{\mu_{HA}\ln I_L(x, y) - \mu_{LA}\ln I_{Hc}(x, y)}{\mu_{HB}\mu_{LA} - \mu_{LB}\mu_{HA}} \qquad (9)$$

FIG. 3D illustrates the afterimage-reduced bone image $d_{BC}(x, y)$ as represented by Formula (9). In the example illustrated in FIG. 3D, the bone density measurement unit 156 calculates an average value of pixel values for the portions L1, L2, L3, and L4 in this order from the top of the lumbar spine 301 in the bone image $d_{BC}(x, y)$ illustrated in FIG. 3D, and measures the bone density [g/cm$^2$] using the calculated average value.
<Step S207>

After the processing of step S206 ends, the processing proceeds to step S207.

In step S207, the display control unit 157 causes the monitor 130, which is the display unit, to display the bone density measured in step S206 via the integrated control unit 110.

After the processing of step S207 ends, the processing in the flowchart illustrated in FIG. 2 ends.

Next, experimental results indicating effects of the present exemplary embodiment will be described.

FIGS. 5A to 5C illustrate the experimental results indicating effects of the exemplary embodiment of the present disclosure.

As illustrated in FIG. 5A, in an experiment, a phantom 500 mimicking the lumbar spine of a human body was used as the subject 20. Specifically, the phantom 500 was formed of polyurethane 510 mimicking the soft tissue, and hydroxyapatite portions 511-1 to 511-3 mimicking the lumbar spine were embedded in the polyurethane 510. Bone densities of the hydroxyapatite portions 511-1, 511-2, and 511-3 were 0.7 [g/cm$^2$], 1.0 [g/cm$^2$], and 1.3 [g/cm$^2$], respectively. In this experiment, a crossed grid with a focal length of 110 cm, a grating density of 52/cm, and a grating ratio of 24:1 was used as the scattered ray removal grid 240. In this case, as illustrated in FIG. 1, the scattered ray removal grid 240 was disposed between the radiation detection apparatus 230 and the subject 20. As imaging conditions, a lower tube voltage for emitting the low-energy (first energy) radiation 221 was set to 80 kV, a higher tube voltage for emitting the high-energy (second energy) radiation 221 was set to 140 kV, a tube current was set to 25 mA, and a pulse width was set to 32 msec. In this experiment, the body thickness dependence was checked by changing the thickness of the phantom 500 to 15 cm, 20 cm, and 25 cm.

FIG. 5B illustrates a comparative example. FIG. 5B is a graph in which the body thickness dependence of each of the three hydroxyapatite portions 511-1 to 511-3, which mimic the lumbar spine that is an ROI, on the phantom 500 in the bone image $d_B$ calculated by using Formula (1) is plotted. At the bone densities of the hydroxyapatite portions 511-1 to 511-3 illustrated in FIG. 5B, the body thickness dependence appears when the thickness of the phantom 500 is 15 cm, 20 cm, and 25 cm, and the variation coefficient thereof is 2.67%. According to the standard for approval of X-ray bone density measurement apparatuses (Apr. 1, 2005, Pharmaceutical and Food Safety Bureau Notification No. 0401050), the variation coefficient of body thickness dependence of a subject is required to be 2% or less. The standard for approval is not satisfied in the example illustrated in FIG. 5B.

FIG. 5C illustrates an exemplary embodiment of the present disclosure. FIG. 5C is a graph in which the body thickness dependence of each of the three hydroxyapatite potions 511-1 to 511-3, which mimic the lumbar spine that is an ROI, on the phantom 500 in the bone image $d_{BC}$ calculated by using Formula (9) is plotted. At the bone densities of the hydroxyapatite portions 511-1 to 511-3 illustrated in FIG. 5C, variations in the body thickness dependence are suppressed compared to the comparative example illustrated in FIG. 5B when the thickness of the phantom 500 is 15 cm, 20 cm, and 25 cm. Specifically, in the exemplary embodiment illustrated in FIG. 5C, the variation coefficient of the body thickness dependence is 0.65%, and it is clear that the variation coefficient satisfies the standard for approval described above.

The image processing unit 150 (image processing apparatus) included in the radiographic imaging system 10 described above performs the following processing. Specifically, the radiographic image obtaining unit 151 obtains the low-energy radiographic image $I_L$ (first radiographic image) obtained by irradiating the subject 20 with the radiation 221 of the low energy (first energy). Next, the radiographic image obtaining unit 151 obtains the high-energy radiographic image $I_H$ (second radiographic image) obtained by irradiating the subject 20 with the radiation 221 of the high energy (second energy) different from the low energy (first energy). Subsequently, the afterimage amount estimation unit 154 estimates the afterimage amount of the low-energy radiographic image $I_L$ in the high-energy radiographic image $I_H$ based on information about the soft tissue region of the subject 20 in the low-energy radiographic image $I_L$ and the high-energy radiographic image $I_H$. Then, the afterimage correction unit 155 corrects the high-energy radiographic image $I_H$ using the afterimage amount estimated by the afterimage amount estimation unit 154.

With this configuration, the afterimage of the low-energy radiographic image $I_L$ (first radiographic image) obtained by the first radiographic imaging in the high-energy radiographic image $I_H$ (second radiographic image) obtained by the second radiographic imaging can be appropriately corrected. Consequently, for example, in the case of measuring the bone density of the subject 20 by the DXA method using the afterimage-corrected high-energy radiographic image $I_H$, it is possible to more desirably measure the bone density by reducing the body thickness dependence of the subject 20.

The present disclosure can also be implemented by executing the following processing in which a program for implementing one or more functions according to the exemplary embodiments described above is supplied to a system or an apparatus via a network or a storage medium, and one or more processors of a computer of the system or the apparatus read and execute the program. The present disclosure can also be implemented by a circuit (e.g., an application-specific integrated circuit (ASIC)) for implementing the one or more functions according to the exemplary embodiments.

The program and a computer-readable storage medium storing the program are included in the present disclosure.

The above-described exemplary embodiments are merely examples of embodiments for carrying out the present disclosure. The technical scope of the present disclosure should not be interpreted in a limited way by the above-described exemplary embodiments. In other words, the present disclosure can be carried out in various ways without departing from the technical idea and the main features thereof.

According to the present disclosure, it is possible to appropriately correct an afterimage of a first radiographic image obtained by first radiographic imaging in a second radiographic image obtained by second radiographic imaging.

Other Embodiments

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2023-104348, filed Jun. 26, 2023, which is hereby incorporated by reference herein in its entirety.

What is claimed is:

1. An image processing apparatus comprising:

an image obtaining unit configured to obtain a first radiographic image and a second radiographic image, the first radiographic image being obtained by irradiating a subject with radiation of a first energy, the second radiographic image being obtained after the first radiographic image by irradiating the subject with radiation of a second energy different from the first energy;

an estimation unit configured to estimate information about an afterimage of the first radiographic image in the second radiographic image based on information about a soft tissue region of the subject in the first radiographic image and the second radiographic image; and a correction unit configured to correct the second radiographic image using the information about the afterimage.

2. The image processing apparatus according to claim 1, wherein the estimation unit obtains information indicating an amount that is proportional to a body thickness of the subject in the soft tissue region as the information about the soft tissue region of the subject and estimates the information about the afterimage using the obtained information.

3. The image processing apparatus according to claim 2, wherein the estimation unit estimates the information about the afterimage using a ratio between information indicating the amount that is proportional to the body thickness of the subject in the first radiographic image and information indicating the amount that is proportional to the body thickness of the subject in the second radiographic image.

4. The image processing apparatus according to claim 3, wherein the image processing apparatus measures a bone density of a bone of the subject using a bone image including the bone of the subject, the bone being different from soft tissue in the soft tissue region, and wherein a first obtaining time interval between the first radiographic image and the second radiographic image is larger than a second obtaining time interval between the first radiographic image and the second radiographic image, the first obtaining time interval being used to obtain the ratio, the second obtaining time interval being used to measure the bone density.

5. The image processing apparatus according to claim 3, wherein during an obtaining time interval between the first radiographic image and the second radiographic image used to obtain the ratio, the image processing apparatus reads an electric signal from a radiation detection apparatus configured to detect the radiation having passed through the subject as the electric signal.

6. The image processing apparatus according to claim 3, wherein the ratio is obtained using a phantom being a model of the subject.

7. The image processing apparatus according to claim 1, further comprising an identifying unit configured to identify the soft tissue region of the subject, wherein the estimation unit obtains information about the soft tissue region of the subject in the first radiographic image and information about the soft tissue region of the subject in the second radiographic image based on the soft tissue region identified by the identifying unit, and estimates the information about the afterimage using the obtained information.

8. The image processing apparatus according to claim 7, wherein the identifying unit identifies, as the soft tissue region of the subject, a designated region on an image displayed on a display screen, the image displayed on the display screen being the first radiographic image, the second radiographic image, or a processed image obtained by performing energy subtraction processing on the first radiographic image and the second radiographic image.

9. The image processing apparatus according to claim 7, wherein the identifying unit identifies the soft tissue region of the subject by performing image processing on the first radiographic image, the second radiographic image, or a processed image obtained by performing energy subtraction processing on the first radiographic image and the second radiographic image.

10. The image processing apparatus according to claim 1, further comprising a measurement unit configured to measure a bone density of a bone of the subject using a bone image including the bone of the subject, the bone being different from soft tissue in the soft tissue region, the bone image being obtained by performing energy subtraction processing on the first radiographic image and the second radiographic image corrected by the correction unit.

11. The image processing apparatus according to claim 10, wherein the measurement unit measures the bone density of the bone using a pixel value for the bone in the bone image.

12. The image processing apparatus according to claim 10, wherein the measurement unit is configured to measure bone densities of a plurality of bones of the subject having a plurality of different body thicknesses.

13. The image processing apparatus according to claim 10, further comprising a display control unit configured to display the bone density measured by the measurement unit on a display unit.

14. The image processing apparatus according to claim 1, wherein the radiation of the second energy is radiation of a higher energy than the radiation of the first energy.

15. A radiographic imaging system comprising:

the image processing apparatus according to claim 1;

a radiation generation apparatus configured to generate the radiation; and a radiation detection apparatus configured to detect the radiation having passed through the subject as an electric signal, wherein the image obtaining unit processes the electric signal to obtain the first radiographic image and the second radiographic image.

16. An image processing method comprising:

obtaining a first radiographic image and a second radiographic image, the first radiographic image being obtained by irradiating a subject with radiation of a first energy, the second radiographic image being obtained after the first radiographic image by irradiating the subject with radiation of a second energy different from the first energy;

estimating information about an afterimage of the first radiographic image in the second radiographic image based on information about a soft tissue region of the subject in the first radiographic image and the second radiographic image; and correcting the second radiographic image using the information about the afterimage.

17. A non-transitory computer-readable storage medium storing a program for causing a computer to execute an image processing method comprising:

obtaining a first radiographic image and a second radiographic image, the first radiographic image being obtained by irradiating a subject with radiation of a first energy, the second radiographic image being obtained after the first radiographic image by irradiating the subject with radiation of a second energy different from the first energy;

estimating information about an afterimage of the first radiographic image in the second radiographic image based on information about a soft tissue region of the subject in the first radiographic image and the second radiographic image; and correcting the second radiographic image using the information about the afterimage.

* * * * *